United States Patent [19]

Iinuma

[11] Patent Number: 4,790,322

[45] Date of Patent: Dec. 13, 1988

[54] ULTRASONIC TYPE BLOOD FLOW AMOUNT MEASURING APPARATUS

[75] Inventor: Kazuhiro Iinuma, Tochigi, Japan

[73] Assignee: Kabushiki Kaisha Toshiba, Kawasaki, Japan

[21] Appl. No.: 888,510

[22] Filed: Jul. 23, 1986

[30] Foreign Application Priority Data

Jul. 24, 1985 [JP]  Japan ............................. 60-164565

[51] Int. Cl.⁴ ............................................. A61B 10/00
[52] U.S. Cl. ............................. 128/661.10; 73/861.25
[58] Field of Search ..................... 128/663, 660–661; 73/861.25

[56] References Cited

U.S. PATENT DOCUMENTS

| 4,257,278 | 3/1981 | Papadofrangakis et al. ..... 73/861.25 |
| 4,265,126 | 5/1981 | Papadofrangakis et al. ..... 73/861.25 |
| 4,501,279 | 2/1985 | Seo ....................................... 128/663 |

FOREIGN PATENT DOCUMENTS 0035213  9/1981  European Pat. Off. ............ 128/663

OTHER PUBLICATIONS

Duran, C. et al, "Recent Progress in Nitral Valve Disease", Butterworths, Boston Mass. ©1984, pp. 16–46.
Fuller, G. et al, "Analytic Geometry and Calculus", Van Nostrand & Co., Princeton, N.J. ©1964, pp. 524–527.
Kasai et al., "Real–Time Two–Dimensional Blood Flow Imaging Using an Autocorrelation Technique," IEEE Transactions on Sonics and Ultrasonics, vol. SU—32, No. 3, May 1985.

Primary Examiner—Francis J. Jaworski
Attorney, Agent, or Firm—Finnegan, Henderson, Farabow, Garrett, & Dunner

[57] ABSTRACT

A blood flow amount measuring apparatus includes an ultrasonic transducer for steering a region of interest of a subject to be measured with an ultrasonic beam and receiving echoes from that region. A Doppler calculation section detects a Doppler signal on a line orthogonal with the steering lines from the echo signal. The speed v of a blood flow on that line at the region of interest is calculated from the Doppler signal and thus and an amount of blood flowing through the region of interest can be evaluated from that speed and area area of the section of that blood flow.

9 Claims, 6 Drawing Sheets

F I G. 1
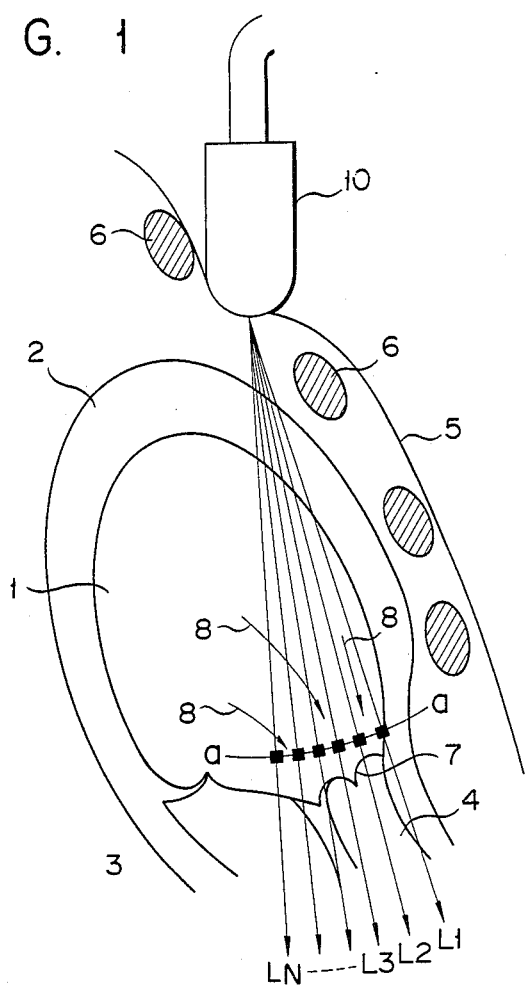
F I G. 2
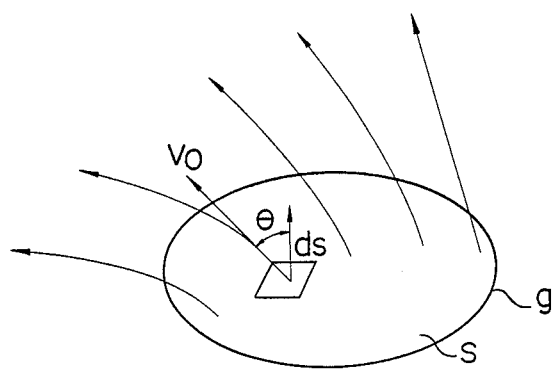

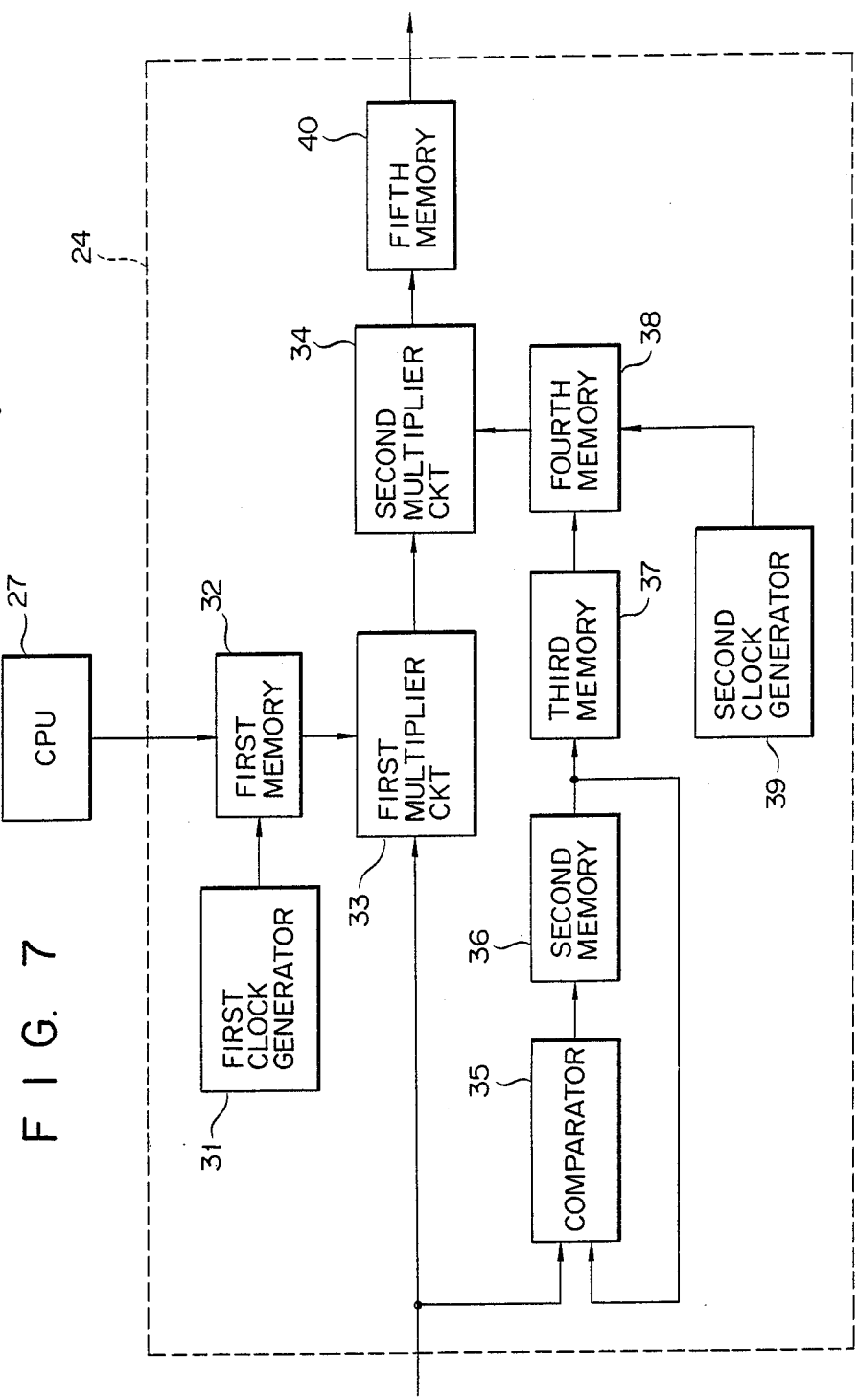
F I G. 7

ULTRASONIC TYPE BLOOD FLOW AMOUNT MEASURING APPARATUS

BACKGROUND OF THE INVENTION

This invention relates to an ultrasonic type blood flow amount measuring apparatus for measuring blood flowing (ml/sec) through a region of interest of a human subject, through the utilization of an ultrasonic Doppler effect.

In a conventional blood flow amount measuring apparatus, utilizing an ultrasonic Doppler effect, an ultrasonic transducer emits an ultrasonic beam of a frequency, fo, to a blood flow in, for example, the blood vessel, in which case the ultrasonic beam emitted is echoed, to be exact, from the blood cell in blood flowing through the blood vessel. At this time the frequency of the echo signal varies in accordance with a blood flow speed due to a Doppler effect resulting from a relative motion between the ultrasonic beam and the bloodstream. With fd representing the Doppler shift frequency of the echo signal of the echo wave at this time a relation between fd and fo as given below holds:

$$fd = \frac{2v'}{C} \cdot fo = \frac{2v\cos\theta}{C} \cdot fo$$
$$v = \frac{C}{2\cos\theta} \cdot \frac{fd}{fo}$$

The angle $\theta$ is an angle between the emission direction of the ultrasonic wave and the direction of the bloodstream. The speed v of the flow of blood is calculated from the aforementioned equation by measuring the angle $\theta$ and thus an amount Q (ml/sec) of blood flow is calculated by multiplying the blood flow velocity v and inner section area S of the blood vessel.

In the conventional blood flow amount measuring apparatus, it is necessary to measure the angle $\theta$ between the direction in which the ultrasonic beam is emitted and the direction in which the blood flows. This angle should be measured, while observing a blood vessel section image on a monitor screen, and the measurement of that angle $\theta$ is very difficult, failing to measure an exact amount of blood flowing through the heart.

SUMMARY OF THE INVENTION

It is accordingly the object of this invention to provide an automatic blood flow amount measuring apparatus for measuring an amount of blood flow without measuring the direction of emission of the ultrasonic beam and that of blood flowed. According to this invention an ultrasonic transducer steers a region of interest of a human subject with an ultrasonic beam and receives an echo from the object. A Doppler calculation unit obtains a Doppler signal on a line orthogonal with the ultrasonic beam from the echo signal. The speed component v of the blood flow along the ultrasonic beam on that line is calculated from the Doppler signal and thus an amount of blood flowed is calculated from the speed component v and section of the blood flow.

Applicant's ultrasonic blood flow amount measuring apparatus comprises ultrasonic transducer means for steering a plurality of ultrasonic beams through a region of interest of subject which has at least one portion through which blood flows converting echoes from said region of interest into echo signals; Doppler signal detecting means for detecting respective Doppler signals from said echo signals delivered from said ultrasonic transducer means, which correspond to the ultrasonic beams; and calculation means coupled to said Doppler signal detecting means, calculating an amount of blood flowing through the region of interest on the basis of the Doppler signals obtained along at least one line orthogonal with the ultrasonic beams.

BRIEF DESCRIPTION OF THE DRAWINGS

FIG. 1 is a view showing an ultrasonic steering for explaining the principle of this invention;

FIGS. 2 to 5 are views for explaining the principle on which this invention is based;

FIG. 7 is a view for showing a circuit diagram of a blood flow calculation section shown in FIG. 6;

DETAILED DESCRIPTION OF THE PREFERRED EMBODIMENTS

Figure 3:
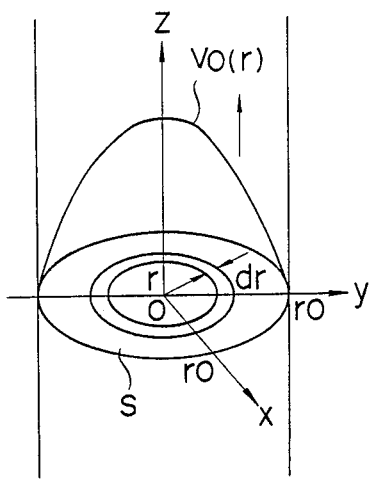

As shown in FIG. 1, ultrasonic transducer 10 is placed in intimate contact with a "breast" wall 5 and emits an ultrasonic beam onto the heart, in a sector steering mode, through a spacing between the ribs 6 of a human being. In this case the ultrasonic beam is transmitted and received an n number of times (for exanple, 8 times) in synchronism with the rate pulses of repetition frequency fr for each of steering lines $L_1, \ldots, L_N$.

Reception signals corresponding to 8 rate pulses in the steering line $L_1$ direction are, after being phase-detected, converted to digital signals from which Doppler signal components are extracted. A Doppler frequency fd is found from the reception information corresponding to the 8 rates and, in this case, it is measured at a time interval (i.e., 800 ns) corresponding to a clock frequency of an A/D converter, for example, 1.25 MHz, along the beam emitted from the ultrasonic transducer. The time interval of 800 ns becomes around 0.6 mm in terms of the distance. That is, the Doppler frequency fd is measured for each of the distances between the sampling points along each steering line. A relation between the Doppler frequency fd at the measuring spot and the blood flow velocity component $v_B$ at the measuring spot in the ultrasonic beam direction is given below:

$$fd = \frac{2v_B}{C} \cdot fo \quad (1)$$

where fo and C, respectively, denote the transmission frequency and sound speed (about 1500 m/s) of the ultrasonic beam. In general, the direction of the ultrasonic beam is different from that of the blood flow and, if an angle $\theta$ represents an angle therebetween with the absolute value of the blood flow speed indicated by $v_O$, then the following Equation (2) holds:

$$v_B = v_O \cdot \cos\theta \quad (2)$$

In relation to the directions of the steering lines $L_1, \ldots L_N$ the corresponding Doppler frequency fd is found at the respective positions.

Suppose that the Doppler frequencies at the intersections of respective ultrasonic beams and line a—a (a circular arc with the ultrasonic transducer as a center in the sector steering) orthogonal with the respective ultrasonic beams are represented by $fd_1, fd_2, \ldots, fd_N$. Then the speed of the bloodstream is increased toward its center and thus the value of the Doppler frequency fd increases toward the center of the blood flow. With the center of the blood flow indicated by an M-th position and the Doppler frequency at this position expressed as $fd_M$, the amount of blood flow can be expressed as follows:

$$Q_A = A \cdot \frac{\pi C}{2fo} \cdot (l \cdot \delta)^2 \sum_{i=1}^{N} (|i - M| + 1) fdi \quad (3)$$

where
- l: the distance from the ultrasonic transducer to the line a—a
- δ: an angle between the adjacent steering lines
- A: a correction coefficient
- fdi: a Doppler shift frequency associated with an i-th steering line.

The solution of Equation (3) represents an amount of blood flowing from left ventricle 1 into aorta 4. The derivation of Equation (3) will be explained below in more detail.

The amount of blood flowing, per unit time, through a region S of interest surrounded by a line g is, in general, a value evaluated by integrating the value of an inner product of a minute area portion in the region S, and the velocity of the blood flow through the minute area portion with respect to the whole region S.

With dS, $V_O$ and $\theta$, respectively, representing the minute area portion, absolute value of the velocity of the blood flow and angle defined between a vertical on the minute area portion and blood flow vector, the amount of blood flow is expressed by the following equation:

$$Q = \int_S v_O \cos \theta \, ds \quad (4)$$

Figure 4:
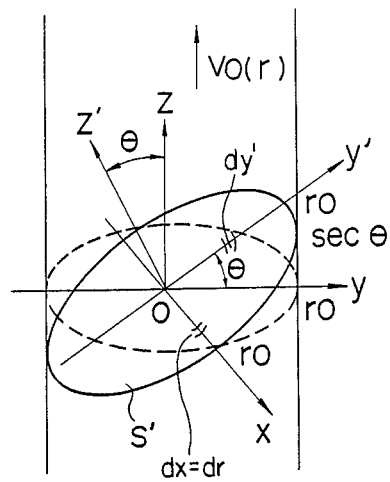

If the blood flows through the blood vessel of a radius ro in the z-axis direction as shown in FIGS. 3 and 4, then the absolute value $v_O(r)$ of the blood flow speed can be expressed as a function of a distance r from the center of the blood vessel.

If a consideration is given to a region or section S orthogonal with the direction of a flow of blood in FIG. 3, an amount of blood flowing through this section is given below:

$$Q_r = 2\pi \int_0^{ro} r \cdot v_O(r) dr \quad (5)$$

Where a consideration is given to a section S' whose y-axis is inclined by an angle $\theta$ with respect to the direction of a flow of blood as shown in FIG. 4, an amount of blood flowing through the section S' in FIG. 4 naturally becomes equal to that flowing through the section S in FIG. 3 if the absolute value $v_O$ of the blood flow speed is the same as that in FIG. 3. Since in FIG. 4 the section or plane S becomes an ellipse, the amount Q of blood flow is, to be exact, evaluated, unlike Equation (5), by a double integral. Here, in Equation (5) for the approximate evaluation of the blood flow, x and y' in FIG. 4 are employed in place of r. In this case, $Q_X$ and $Q_{Y'}$ are defined by the following Equations (6) and (7).

$$Q_X = 2\pi \int_0^{ro} x \cdot v_O(x) \cos\theta \, dx \quad (6)$$
$$= 2\pi \cos\theta \int_0^{ro} r v_O(r) dr$$
$$= Q_r \cdot \cos\theta$$

$$Q_{Y'} = 2\pi \int_0^{ro \sec\theta} y' \, v_O(r') \cos\theta \, dy' \quad (7)$$

Since $y' = r \cdot \sec\theta$, then $Q_{Y'}$ can be rewritten as follows:

$$Q_{Y'} = 2\pi \int_0^{ro} r \cdot \sec\theta \cdot v_O(r) dr \quad (8)$$
$$= 2\pi \sec\theta \cdot \int_0^{ro} r v_O(r) dr$$
$$= Q_r \cdot \sec\theta$$

From Equations (6) and (8), Qr is found by the following Equation (9):

$$Q_r = \sqrt{Q_X \times Q_{Y'}} \quad (9)$$

Where $\theta$ is adequately smaller than 1, Qr can be evaluated from the following Equation (10):

$$Q_r = \frac{Q_X + Q_{Y'}}{2} \quad (10)$$

Even where the section S' is not perpendicular to the direction of the flow of blood, the amount of blood flow can be approximately evaluated, with the use of Equation (10), by one-dimensionally integrating the major and minor axes of that section. For an axisymmetric blood flow, if the section is vertical with respect to blood flow, the amount of blood flow can be evaluated from Equation (5). Thus, an amount of blood flowing through that section axisymmetrically inclined with respect to the blood flow can be evaluated from the value of the major or minor axis or an average value of both.

In the bloodstream through the heart in FIG. 1, blood flows, as a cardiac output, from left ventricle 1 into aorta 4 in the systolic cycle. If, for example, the line a—a is a line of adequately great length as seen from the left ventricle 1 side immediately before aorta valve 7, the blood passes through the region including the line a—a.

Figure 5:
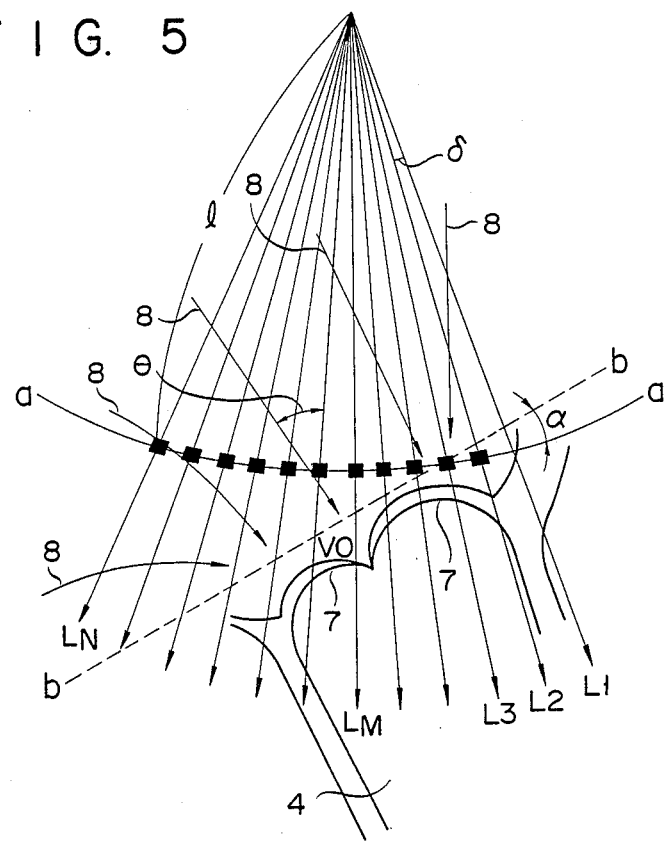

In FIG. 5, $v_O(r)$ shows the absolute value of a blood flow speed at the intersections of steering lines $L_1$ to $L_N$, and line a—a, where r represents a distance measured from a center position M corresponding to the highest blood flow speed among the intersections. The minute portion defined in the r direction perpendicular to the steering direction is indicated as dr and an angle between the blood flow speed vector 8 and the steering line is indicated by $\theta$. Under this condition the amount of blood flow is evaluated by the following equations.

Equation (11) is obtained with respect to a section through the major axis of the heart.

$$Q_{\|} = \pi \int_{a-a} \cdot r \cdot v_0(r)\cos\theta dr \tag{11}$$

$\theta$ represents an angle between the ultrasonic beam and the blood flow vector 8. $Q_{\|}$ is evaluated from the following Equation (12) by substituting Equations (1) and (2) into Equation (11).

$$Q_{\|} = \pi \cdot \frac{C}{2fo} \cdot \int_{a-a} \cdot r \cdot fd(r)dr \tag{12}$$

dr is replaced by a distance between the steering lines on the line a—a and is calculated from Equation (13). In this case, l denotes a distance from the ultrasonic transducer to the line a—a and $\delta$ represents an angle between the adjacent steering lines.

$$dr = l \cdot \delta \tag{13}$$

Substituting Equation (13) into Equation (12) yields an equation given below:

$$Q_{\|} = \pi \cdot \frac{C}{2fo} \cdot \sum_{i=1}^{N} \{(|i - M| + 1)l \cdot \delta\} fdi \cdot (l \cdot \delta) \tag{14}$$
$$= \pi \cdot \frac{C}{2fo} \cdot (l \cdot \delta)^2 \cdot \sum_{i=1}^{N} (|i - M| + 1)fdi$$

When the line a—a is rotated with the center steering line M as an axis, an amount $Q_1$ at a circular arc a'—a' as expressed by the following Equation (15) is evaluated. Provided that $\alpha$ represents an angle between the line a—a and line b—b, substantially parallel to aorta valve 7 and perpendicular to an axis of aorta 4, as a value at a center position, then $$Q_1 = \cos\alpha \cdot \pi \int_{a'-a'} \cdot rV_0'(r)\cos\theta dr \tag{15}$$

$$Q_\perp = \pi \cdot \frac{C}{2fo} \cdot (l \cdot \delta)^2 \cdot \sum_{i=1}^{N} (|i - M| + 1)fdi' \tag{16}$$

Thus the amount Q of blood flow is obtained from the following equation:

$$Q = \frac{Q_{\|} + Q_\perp}{2} \tag{17}$$

Where $\alpha$ is smaller, then Q can be obtained as follows:
$$Q \approx Q_{\|} \approx Q_\perp \tag{18}$$

It may be considered that the blood flowing from left ventricle 1 into aorta 4 becomes substantially axisymmetric at the left ventricle side (left ventricle exit). In this case, however, such a symmetry is not necessarily adequate and thus it is necessary to somewhat correct the amount of blood flow. With this correction factor indicated by A, the amount of blood flow can be evaluated in the same equation as Equation (3). A is a value approximate to unity and is determined based on clinical data, noting that this may be considered as being within a range of $0.5 < A < 2$.

In a blood flow passage having a large section, such as the cardiac cavity, the amount of blood flow can be properly evaluated from Equation (3). In a passage such as a blood vessel which is smaller in section and whose section is covered within the width of the ultrasonic beam, on the other hand, the amount of blood flowing through the blood vessel can be calculated from an equation given below:

$$Q_L = L \cdot \frac{C}{2fo} \cdot (l \cdot \delta)D \sum_{i=1}^{N} fdi \tag{19}$$

where
D: the diameter of the blood vessel
L: the correction factor

The embodiment of this invention will now be explained below on the aforementioned principle.

Figure 6:
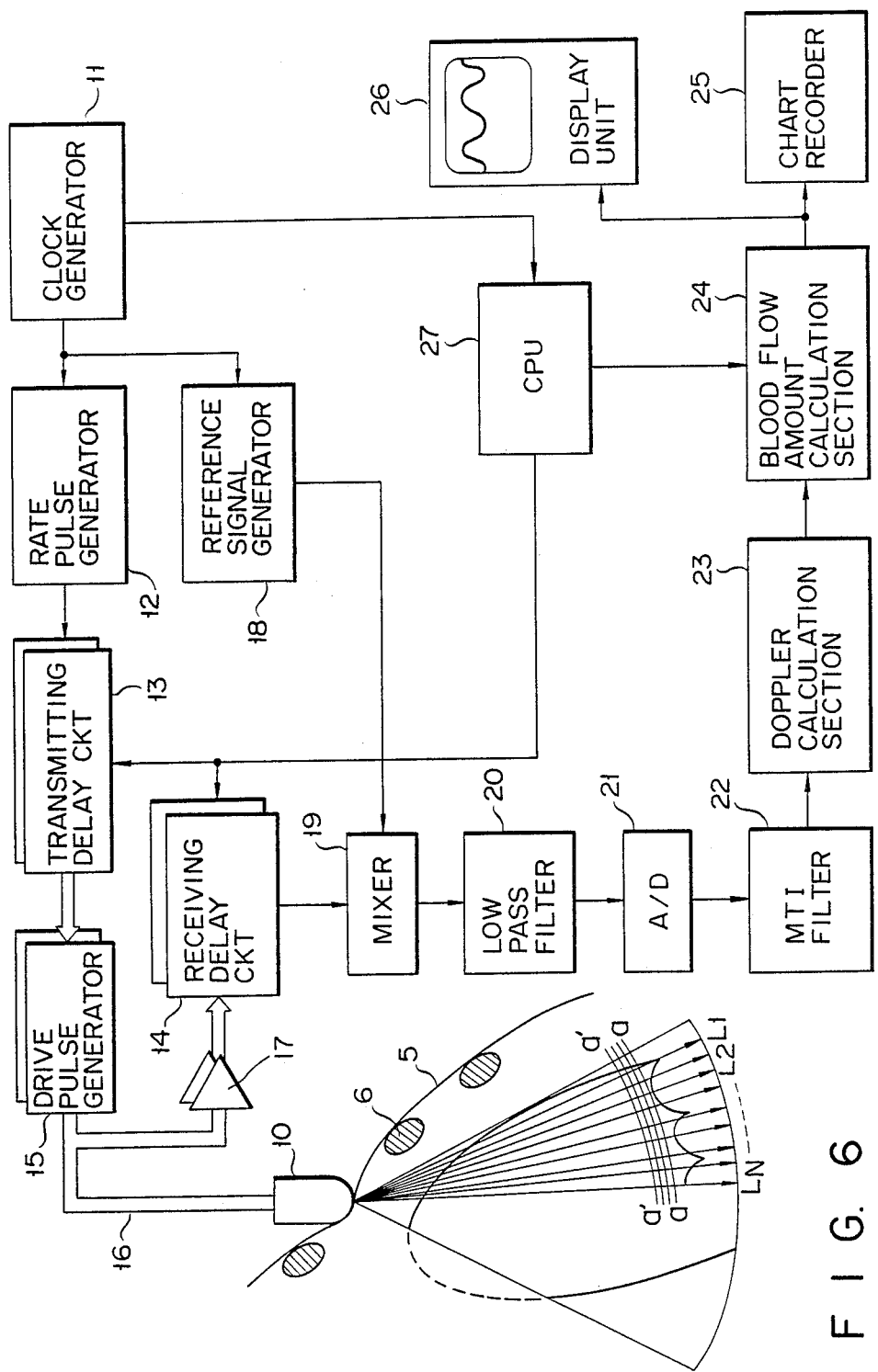
FIG. 6 is a view showing an ultrasonic type blood flow amount measuring apparatus according to one embodiment of this invention.
Figure 8:
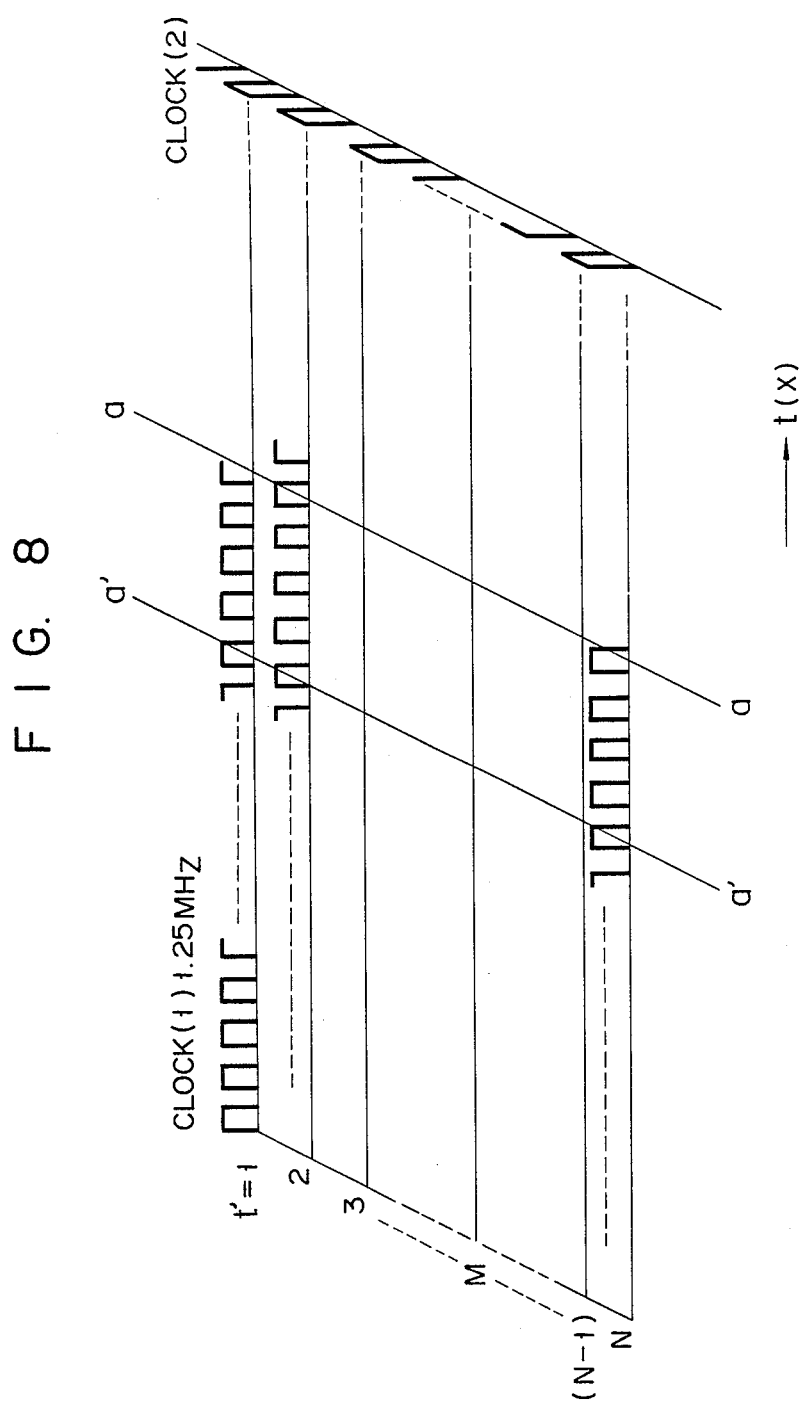
FIG. 8 shows a time chart showing a drive pulse.

In the embodiment shown in FIG. 6, clock generator 11 delivers a fundamental clock of, for example, 40 MHz to rate pulse generator 12, which in turn delivers a rate pulse of 5 KHz, on the basis of the fundamental clock of clock generator 11, to transmitting delay circuit 13. Delay circuit 13 serves to delay the pulse rate in accordance with the steering direction and is connected to drive pulse generator 15. Drive pulse generator 15 is comprised of a plurality of pulsers which are connected to an ultrasonic transducer through cable 16.

Ultrasonic transducer 10 is driven by the drive pulse of the pulser and transmits an ultrasonic beam to the region of interest and receives echoes from the object. The echo signal from ultrasonic transducer 10 is connected through amplifier 17 to receiving delay circuit 14. Delay circuit 14 is set to a delay time corresponding to the delay time of delay circuit 13 and extracts a reception signal corresponding to the respective steering line. The output of delay circuit 14 is connected to mixer 19 which in turn detects a reception signal through the multiplication of a reference signal (for example, 2.5 MHz) of reference signal generator 18 and reception signal of delay circuit 14. Mixer 19 is comprised of a 2-channel mixer circuit so as to find the normal and reverse directions of a Doppler signal from the reception signal. The same reception signals are supplied to both of the channels of the 2-channel mixer circuit, noting that reference signals whose phases are exactly 90° shifted with respect to each other are supplied to reference input terminals of the two-channel mixer circuit.

The output terminal of mixer 19 is connected to MTI (Moving Target Indication) filter 22 through low-pass filter 20 and A/D converter 21. Low-pass filter 20 is provided to remove an unwanted high-pass component from the signal of mixer 19. MTI filter 22 is provided to eliminate an echoed wave component which comes from a slow motion region such as the cardiac muscle. The output terminal of MTI filter 22 is connected to Doppler calculation section 23 for calculating a Doppler shift frequency fd. The output terminal of Doppler calculation section 23 is connected to blood flow amount calculation section 24. Based on the Doppler frequency signal from Doppler calculation section 23, blood flow amount calculation section 24 evaluates, with the use of Equations (3) and (17) or (19), the value of the frequency fd of a Doppler signal which is obtained for each given distance from the surface of a human body or for each given time interval from the generation of a rate pulse. Blood flow amount calculation section 24 is connected at its output to chart recorder 25 and to display 26. It is to be noted that CPU 27 controls blood flow amount calculation section 24 and transmitting and receiving delay circuits 13 and 14.

As shown in FIG. 7, blood flow amount calculation section 24 includes first memory 32 for permitting a later-described factor which is input from CPU 27 to be stored in response to the clock of first clock generator 31. First memory 32 is connected at its output terminal to first multiplier circuit 33 and Doppler calculation section 23 is connected at its output terminal to the other input terminal of multiplier circuit 33. First multiplier circuit 33 is connected to one input terminal of second multiplier circuit 34.

Comparator 35 compares the output of second memory 36 with Doppler shift frequency fd which has been calculated by Doppler calculation section 23. Second memory 36 is connected to the output terminal of comparator 35 so that it stores a result of a comparison by comparator 35. The output terminal of second memory 36 is connected to the input terminal of third memory 37. Third memory 37 stores number data of the steering line corresponding to Doppler frequency data in second memory 36. The output terminal of third memory 37 is connected to the input terminal of fourth memory 38 which stores a value $|i-M|$. The stored value is read onto second multiplier circuit 34 in response to a clock of second clock generator 39. Second multiplier circuit 34 multiplies the output of first multiplier circuit 33 and output of fourth memory 38 and delivers a signal, as a result of multiplication, to fifth memory 40. Fifth memory 40 is connected at its output terminal to chart recorder 25 and to display 26.

The operation of the aforementioned automatic blood flow amount measuring apparatus will now be explained below.

A clock is delivered from clock generator 11 to rate pulse generator 12 which in turn generates a rate pulse of 5 KHz on the basis of the clock. Rate pulse generator 12 supplies the rate pulse to transmitting delay circuit 13 where it is delayed at a delay time determined in the sector steering direction ($L_1$ to $L_N$). The delayed rate pulse is supplied to drive pulse generator 15 which delivers a drive pulse corresponding to that delay time. The drive pulse is supplied to ultrasonic transducer 10 which emits a corresponding ultrasonic beam in the direction of the steering line $L_1$. The ultrasonic beam travels into the heart and at this time the echoes from that living tissue sequentially enter into ultrasonic transducer 10 in accordance with the depth of the living tissue. Ultrasonic transducer 10 converts the echoes into echo signals.

The echo signals are, after being amplified by amplifier 17, supplied to receiving delay circuit 14 where they are sequentially delayed by a delay time equal to that of transmitting delay circuit 13. At this time the echo signals are added together. The output signal of receiving delay circuit 14 is input to mixer 19 where it is phase-detected. The output signal of receiving delay circuit 14 is amplitude detected, by an amplitude detection circuit not shown, and then enters into the display unit where it is displayed as a B mode.

The echo signal is, after being phase detected by mixer 19, supplied through low-pass filter 20 to A/D converter 21. A/D converter 21 converts the echo signal to a DC one in response to a clock with a frequency of 1.25 MHz. The sampling of the echo signal at 1.25 MHz is analogous to sampling the echo signal for every 0.6 mm as seen in the depth direction from the surface of the region of interest with the sound speed calculated as 1500 m/s in terms of its distance.

When one cycle of the transmission and reception of the ultrasonic beam is completed, then the next cycle is similarly performed. In this way, eight cycles of such transmission and reception operations are effected in the steering direction ($L_1$) so that eight echo data are picked up, at an interval of 0.6 mm apart, in the respective positions of the region of interest.

The echo data obtained at the steering line $L_1$, after being filtered by the MTI filter, are entered into Doppler calculation section 23. Doppler calculation section 23 evaluates the Doppler shift frequency fd, from the echo data so picked up, on the basis of Equations (1) and (2). The shift frequency (fd) data as a result of the calculation is delivered to blood flow amount calculation section 24 where the amount of blood flowed is calculated from the shift frequency (fd) data with the use of Equation (3) or (19) to permit an evaluation of fd, i.e., $fd_1$ at the junction of the steering line $L_1$ and line a—a defined in the direction orthogonal with the steering line $L_1$.

If $fd_1$ at the aforementioned junction is so evaluated, then $fd_2$ at the junction of the steering line $L_2$ and line a—a is evaluated in the similar way as set forth above. In this way the amounts of blood flowing at the junctions of the steering lines $L_1$ to $L_2$ and aforementioned line a—a are evaluated in the sequential fashion. The amounts of blood flowing at these junctions are added together to permit an amount of blood flowing from the heart into the aorta to be evaluated from this addition value.

In the evaluation of the amount of blood in relation to the line a—a, the Doppler data is picked up from, for example, 256 positions across the depth of the region of interest at an interval 0.6 mm apart. If the Doppler data is picked up in relation to, for example, eight lines a—a to a'—a', an amount of blood flow can more exactly be calculated from an average value of amounts of blood flow in relation to the eight lines. Let it be assumed that, for example, the ultrasonic beam is repeatedly transmitted and received at a pulse rate frequency of 5 KHz with the number of steering lines, N, as 16 and the one steering line as eight rates. Since in this case one data per 25.6 ms in relation to one line a—a, i.e., 39 data per second are obtained from blood flow amount calculation section 24, if data is picked up in relation to the eight lines a—a to a'—a', then 8-fold data can be obtained over the same internal as in the case of one line.

Equations (3) and (19), comprised of a combination of a sum and product, can be calculated rapidly, but the processing speed can be improved more if the following procedure is employed. The values A, $\pi$, C, fo and $\delta$ in Equation (3) are determined as known ones irrespective of the amount of blood flowing at the region of interest. l is regarded as being constant, while measuring the amount of blood flow, by designating the line a—a. Thus it is not necessarily required that the aforementioned factors be rapidly calculated in real time. It is only necessary to evaluate the amount of blood flow, by virtue of CPU 27, through the initial calculation of Equation (20) below and substitution of a result of calculation, B, into Equation (21) given below:

$$B = A \cdot \pi \cdot \frac{C}{2fo} \cdot (l \cdot \delta)^2 \tag{20}$$

$$Q_A = B \sum_{i=1}^{N} (|i - M| + 1) fd_i \tag{21}$$

noting that the calculation of Equation (21) is performed through the use of the circuit of FIG. 7.

The operation of the circuit of FIG. 7 will now be explained below:

The circuit of FIG. 7 is responsive to a clock whose Doppler frequency fd is 1.25 MHz, to pick up Doppler data at positions across the depth of the region of interest at an interval of 0.6 mm, i.e. 0.8 μs, in the steering line $L_1$ direction of FIG. 1. At fd=256, Doppler frequency data ($fd_1^1, fd_1^2, \ldots, fd_1^{256}$) are obtained over a distance of 15.4 cm for a time period of 0.8 μs×256≈205 μs. The Doppler frequency data is input to first calculation circuit 33 where it is multiplied by the factor B which is read out from first memory 32. The factor B contains a distance l from ultrasonic transducer 10 and the distance l is increased at a rate of 0.6 mm for every clock pulse of 1.25 MHz from first clock generator 31. The output of Doppler calculator 23 is compared with the output of second memory 36 by virtue of comparator 35. When the output of Doppler calculation section 23 is greater than that of second memory 36, second memory 36 is updated to the Doppler frequency data of Doppler calculation section 23. Since second memory 36 is initially set in a "0" state, data $fd_1^1, fd_1^2, \ldots, fd_1^{256}$ corresponding to an initially input steering line (i=1) are stored in second memory 36.

Next, data corresponding to the steering line $L_2$ are input to comparator 35 at which time the data fd alone greater than the data on the previously stored steering line $L_1$ is stored in second memory 36. The steering line number i corresponding to data written into second memory 36 is stored in third memory 37. A value $|i-M|$ is written into four memory 38 where it varies from 1 to N in response to the clock from second clock circuit 39. The value M is initially set in an N/2 or (N+1)/2 state, but upon the completion of one steering (i=1 to N) the value M is stored in third memory 37 so that it is written into fourth memory 38. The contents of fourth memory 38 are updated each time a section of a region of interest is steered.

At the first rate 256 data $Bfd_1^1, Bfd_1^2, \ldots, Bfd_1^{256}$ are sequentially delivered at an interval of 0.8 μs to second multiplier circuit 34 to permit a multiplication to be made between the output of first multiplier circuit 33 and the data $|1-M|$ stored in fourth memory 38. The result of multiplication is stored in fifth memory 40. At the second rate, first multiplier circuit 33 delivers the data $Bfd_2^1, Bfd_2^2, \ldots, Bfd_2^{256}$ to second multiplier circuit 34 where multiplication is made, as in the case of the first rate, between these data and the data $|2-M|$ from fourth memory 38. The result of the multiplication is supplied to fifth memory 40 where it is added to the first rate data. In this way, calculations are made up to the N-th rate to obtain a calculation output of Equation (21). This means that Equation (3) has eventually been evaluated.

The calculation result data stored in fifth memory 40 is supplied to chart recorder 25 and to display unit 26 for display.

Since it takes 25.6 ms to effect the calculation up to the N-th rate a corresponding amount of blood flow can be evaluated for every 25.6 ms and displayed on the display unit. The cardiac output can be calculated by either calculating an average amount of blood flowed or integrating an amount of blood flowing per heart stroke or beat and multiplying this integrated value by the heart rate.

As set out above, the Doppler signals are detected from waves echoed on the region of interest as a result of emission of the ultrasonic beam and thus the Doppler signals on the line defined in a direction orthogonal with the steering line of the ultrasonic beam are calculated with the result that not only an amount of blood flowing through the blood vessel for instance but also an amount of blood flowing through one of the inner organs whose blood flow direction is not definite, such as the heart, can automatically be measured in real time and be displayed as a measured value on the display unit. It is also possible to simultaneously observe the motion of the heart and spatial state of bloodstream in the heart. Since an ordinary ultrasonic section image, i.e., B mode image can be displayed according to this invention, the amount of blood flowing in the region of interest can be measured, while observing the B mode, thus offering very valuable diagnostic information to the doctor.

Figure 9:
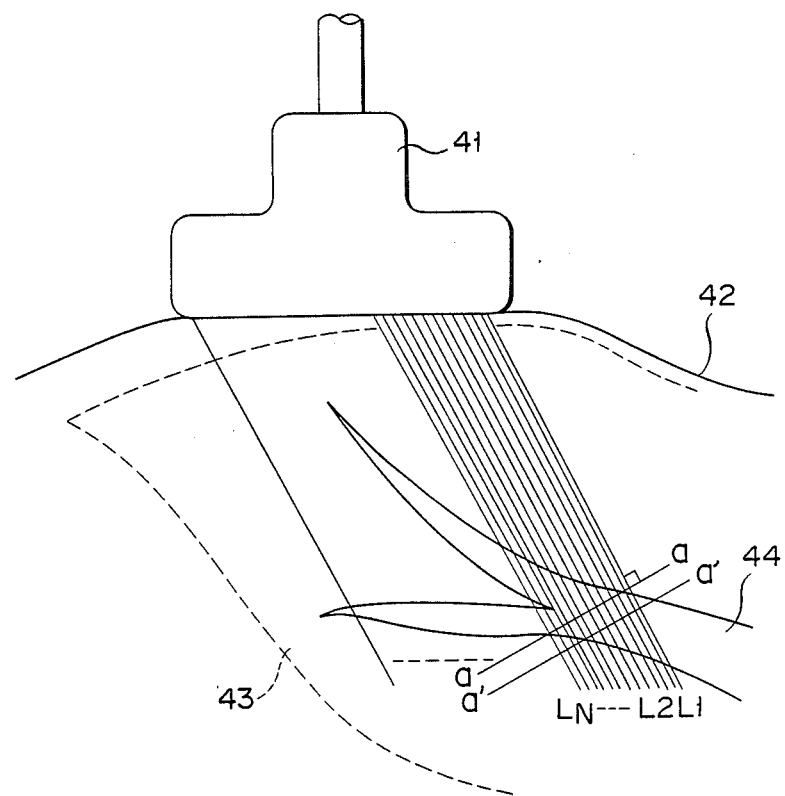
FIG. 9 is a schematic view showing an apparatus utilizing a linear steering.

Although in the aforementioned embodiment the amount of blood flowed can be measured in the sector steering mode, an amount of blood flowing in a carotid or an abdominal blood vessel or a fetus can be measured if a diagonal steering is carried out with the use of a linear array transducer. That is, as shown in FIg. 9, linear array transducer 41 is placed in intimate contact with surface 42 of a human subject to be examined and an ultrasonic beam is emitted into the liver 43 containing the hepatic veins 44 in a linear steering mode. The amount of blood flowing through the hepatic veins can be measured by, while observing the B mode image displayed in real time with the use of echo signals, setting the lines a—a to a'—a' defining diagonals with the lines $L_1$ to $L_N$ in the B mode. In this case, the amount of blood flow there is evaluated based on the following equation:

$$Q_A = A \cdot \pi \cdot \frac{C}{2fo} \cdot d^2 \sum_{i=1}^{N} (|i - M| + 1) fd_i \tag{22}$$

where d: a distance between the steering lines in a linear steering mode.

Although in the aforementioned embodiment the amount of blood flow has been explained as being evaluated in one direction, i.e., in a direction orthogonal with the steering line, an amount of blood flow can also be calculated in a second direction orthogonal with said one direction so that a whole amount of blood may be evaluated based on both the lines. Even if steering is made across the depth of a region of interest, i.e., across the center or near center of the region, through which the whole blood flows, with the use of the ultrasonic beam, or even if steering is made across a portion of the region of interest, it is yet possible to evaluate the whole amount of blood flowing there.

What is claimed is:

1. An ultrasonic blood flow amount measuring apparatus comprising:
    ultrasonic transducer means for steering a plurality of ultrasonic beams through a region of interest of a subject which has at least one portion through which blood flows converting echoes from said region of interest into echo signals;

Doppler signal detecting means for detecting respective Doppler signals from said echo signals delivered from said ultrasonic transducer means, which correspond to the ultrasonic beams; and calculation means coupled to said Doppler signal detecting means, for calculating an amount of blood flowing through the region of interest on the basis of the Doppler signals obtained along at least one line orthogonoal with the ultrasonic beams.

2. An ultrasonic blood flow amount measuring apparatus according to claim 1, wherein said ultrasonic transducer means is comprised of means for sector-steering said region of interest of said subject and said calculation means calculates said amount of blood by calculating the following equations:

$$Q_A = B \cdot \sum_{i=1}^{N} (|i - M| + 1)fdi$$

$$B = A \cdot \pi \cdot \frac{C}{2fo} \cdot (l \cdot \delta)^2$$

where
A: a correction coefficient
C: the sound speed of said ultrasonic beam
fo: the frequency of said ultrasonic beam
l: a distance from said ultrasonic transducer to the line orthogonal with the ultrasonic beams
δ: an angle between any adjacent two of the ultrasonic beams
i: the number of each of the ultrasonic beams
N: the number of ultrasonic beams
M: the number of a central one of the ultrasonic beams
fdi: a Doppler shift frequency associated with an i-th one of the ultrasonic beams.

3. An ultrasonic blood flow amount measuring apparatus according to claim 1, wherein said ultrasonic transducer means is comprised of means for scanning said region of interest of said subject in one direction orthogonal with the ultrasonic beams.

4. An ultrasonic blood flow amount measuring apparatus according to claim 1, wherein said ultrasonic transducer means is comprised of means for scanning, with said ultrasonic beam, said region of interest of said subject in one direction orthogonal with the ultrasonic beams and in another direction intersecting said one direction.

5. An ultrasonic blood flow amount measuring apparatus according to claim 1, wherein said Doppler signal detecting means detects the Doppler signals corresponding to a plurality of lines orthogonal with said ultrasonic beams, and said calculation means is comprised of means for calculating said amount of blood flowing through said region of interest of said subject on the basis of the Doppler signals corresponding to the lines orthogonal with said ultrasonic beams.

6. An ultrasonic flow amount measuring apparatus according to claim 6, wherein said calculation means is comprised of means for calculating an average of amounts of blood which correspond to the lines orthogonal with said ultrasonic beams.

7. An ultrasonic blood flow amount measuring apparatus according to claim 1, wherein said ultrasonic transducer means is comprised of means for linearly scanning said region of interest of said subject and said calculation means calculates an amount of blood flow by evaluating the following equation:

$$Q_A = A \cdot \pi \cdot \frac{C}{2fo} \cdot d^2 \sum_{i=1}^{N} (|i - M| + 1)fdi$$

where
A: a correction coefficient
C: the sound speed of the ultrasonic beam
d: a distance between ultrasonic beams
fo: the frequency of the ultrasonic beam
i: the number of each of the ultrasonic beams
M: the number of a central one of said ultrasonic beams
N: the number of ultrasonic beams
fdi: a Doppler shift frequency associated with an i-th one of the ultrasonic beams.

8. An ultrasonic blood flow amount measuring apparatus according to claim 1, wherein said calculation means claculates said amount of blood flow according to the following equation:

$$Q_A = A \cdot \pi \cdot \frac{C}{2fo} \cdot (l \cdot \delta)^2 \sum_{i=1}^{N} (|i - M| + 1)fdi$$

where
A: a correction coefficient
C: the sound speed of said ultrasonic beam
fo: a transmission frequency of the ultrasonic beam
l: a distance from said ultrasonic transducer means to the line orthogonal with the ultrasonic beams
δ: an angle defined by adjacent two of the ultrasonic beams
i: the number of each of the ultrasonic beams
M: the number of a central one of the ultrasonic beams
N: the number of ultrasonic beams
fdi: a Doppler shift frequency associated with an i-th one of the ultrasonic beams.

9. An ultrasonic blood flow amount measuring apparatus comprising:
ultrasonic transducer means for scanning a region of interest of a subject through which blood flows, employing a plurality of ultrasonic beams, and for converting echoes from said region of interest into echo signals;

Doppler signal detecting means for detecting Doppler signals from said echo signals delivered from said ultrasonic transducer means, said Doppler signals corresponding to the plurality of ultrasonic beams, respectively; and calculation means coupled to said Doppler signal detecting means, for calculating an amount of blood flowing through the region of interest on the basis of the Doppler signals obtained along at least one line orthogonal with the ultrasonic beams.

* * * * *